(12) United States Patent
Cheney

(10) Patent No.: US 8,777,927 B2
(45) Date of Patent: Jul. 15, 2014

(54) APPARATUS AND SYSTEM FOR ADMINISTERING MEDICATION

(76) Inventor: Ronald A. Cheney, Carroll, IA (US)

(*) Notice: Subject to any disclaimer, the term of this patent is extended or adjusted under 35 U.S.C. 154(b) by 358 days.

(21) Appl. No.: 13/030,607

(22) Filed: Feb. 18, 2011

(65) Prior Publication Data

US 2012/0215198 A1 Aug. 23, 2012

(51) Int. Cl.
*A61M 25/00* (2006.01)

(52) U.S. Cl.
USPC ............ 604/523; 604/512; 604/508

(58) Field of Classification Search
CPC ............ A61M 16/0463; A61M 16/0486; A61M 19/00; A61M 25/0026; A61M 25/0028; A61M 25/0029; A61M 25/003; A61M 2025/0057
USPC ............ 604/39–45, 264, 500, 508–517, 523, 604/173
See application file for complete search history.

(56) References Cited

U.S. PATENT DOCUMENTS

| | | | | |
|---|---|---|---|---|
| 3,726,281 | A | * | 4/1973 | Norton et al. .......... 604/43 |
| 5,250,038 | A | * | 10/1993 | Melker et al. ......... 604/264 |
| 5,405,334 | A | * | 4/1995 | Roth et al. ........... 604/264 |
| 5,788,680 | A | | 8/1998 | Linder |
| 6,050,986 | A | * | 4/2000 | Hektner ................ 604/508 |
| 6,162,202 | A | * | 12/2000 | Sicurelli et al. ...... 604/272 |
| 6,592,544 | B1 | * | 7/2003 | Mooney et al. ........ 604/43 |
| 6,802,823 | B2 | | 10/2004 | Mason |
| 6,858,019 | B2 | * | 2/2005 | McGuckin et al. ... 604/43 |
| 2001/0044619 | A1 | * | 11/2001 | Altman ................. 604/539 |
| 2005/0137577 | A1 | | 6/2005 | Heruth et al. |
| 2009/0198248 | A1 | * | 8/2009 | Yeung et al. .......... 606/108 |

* cited by examiner

*Primary Examiner* — Kami A Bosworth
(74) *Attorney, Agent, or Firm* — Zarley Law Firm, P.L.C.

(57) ABSTRACT

A method and apparatus for administering medication. The method and apparatus includes providing a treatment tube having a wall with an exterior surface and a central lumen. The treatment tube also includes at least one hollow tubular channel disposed within the wall of the treatment tube. Medication is delivered supplied to the hollow tubular channel and delivered through the wall of the treatment tube to the exterior surface of the treatment tube.

18 Claims, 8 Drawing Sheets

APPARATUS AND SYSTEM FOR ADMINISTERING MEDICATION

BACKGROUND OF THE INVENTION

This invention relates to an apparatus and system for administering medication. More specifically, this invention is directed to an apparatus and system for the delivery of a constant flow of site-specific medication to pain-sensitive membranes when intubated by tubing foreign to the body.

The utilization of tubes and catheters including but not limited to nasogastric tubes, Foley catheters, chest tubes, and various cavity drains such as abdominal drains is prevalent in modern medicine. These devices perform important functions such the administration of drugs, food, or oral agents such as activated charcoal into a patient's stomach, the drainage of urine from a patient's bladder, or the removal of air, fluid, and/or pus from a patient's intrathoracic space, respectively, either individually or as a requisite component of a wide variety of patient treatment protocols. Despite the widespread use, efficacy, and the essential functions these devices perform in the treatment of patients, nasogastric tubes, Foley catheters, chest tubes, cavity drains and the like can present a considerable disadvantage in terms of patient comfort as these tubes can be irritating and painful to surrounding pain-sensitive tissues of membranes such as the pleural, peritoneum, and mucous membranes of the oral pharynx and urethra.

Body cavities such as the oral pharynx, urethra, pleural and peritoneum include interstitial tissues and membranes which are highly sensitive to pain. When these interstitial membranes and tissues are intubated with tubing foreign to the body by the insertion of a nasogastric tube, Foley catheter, chest tube, cavity drain or the like into a patient's body cavity, these tubes and catheters not only necessarily engage and disturb the patient's pain-sensitive mucous membranes or body cavity tissues, but also are often positioned to lie in direct contact with such pain sensitive tissues and membranes for prolonged amounts of time, thus causing the patient a significant amount of perceived discomfort and pain. As a result, a need has arisen to confront and alleviate the pain and discomfort caused by the often prolonged contact between foreign tubes and/or catheters and pain-sensitive membranes.

Traditional efforts, such as systemic medications, have been employed in an attempt to control the pain associated with such tubing and catheters. However, doing so has proven difficult and is of limited effectiveness in terms of pain control, particularly because systemic medications are not administered directly to the tissues and membranes at the site of the perceived pain, and thus, systemic medications fail to target the source of the discomfort and are unable to effectively treat and directly alleviate the pain perceived by the pain sensitive membranes. Therefore, a need exists to provide an apparatus and system for administering medication which alleviates the pain and discomfort associated with the intubation of tubing foreign to the body that overcomes these problems.

Therefore, a principal object of the invention is to provide an apparatus and system for administering medication which provides a continuous flow of site-specific pain medication directly to the source of the pain caused by a foreign body.

It is yet another object of this invention to provide an apparatus and system for administering medication which decreases the surface area of the tube in contact with the pain sensitive membranes.

It is still another object of this invention to provide an apparatus and system for administering medication which provides effective, targeted, and responsive pain control.

It is a further object of this invention to provide an apparatus and system for administering medication which provides a greater degree of contact and distribution between the pain sensitive membranes and the pain medication.

These and other objects, features or advantages of the present invention will become apparent from the specification and claims.

BRIEF SUMMARY OF THE INVENTION

A method and apparatus for administering medication includes providing a treatment tube having a wall with an exterior surface and a central lumen. The treatment tube also includes at least one hollow tubular channel disposed within the wall of the treatment tube. Medication is delivered supplied to the hollow tubular channel and delivered through the wall of the treatment tube to the exterior surface of the treatment tube.

DETAILED DESCRIPTION OF THE PREFERRED EMBODIMENT

Figure 1:
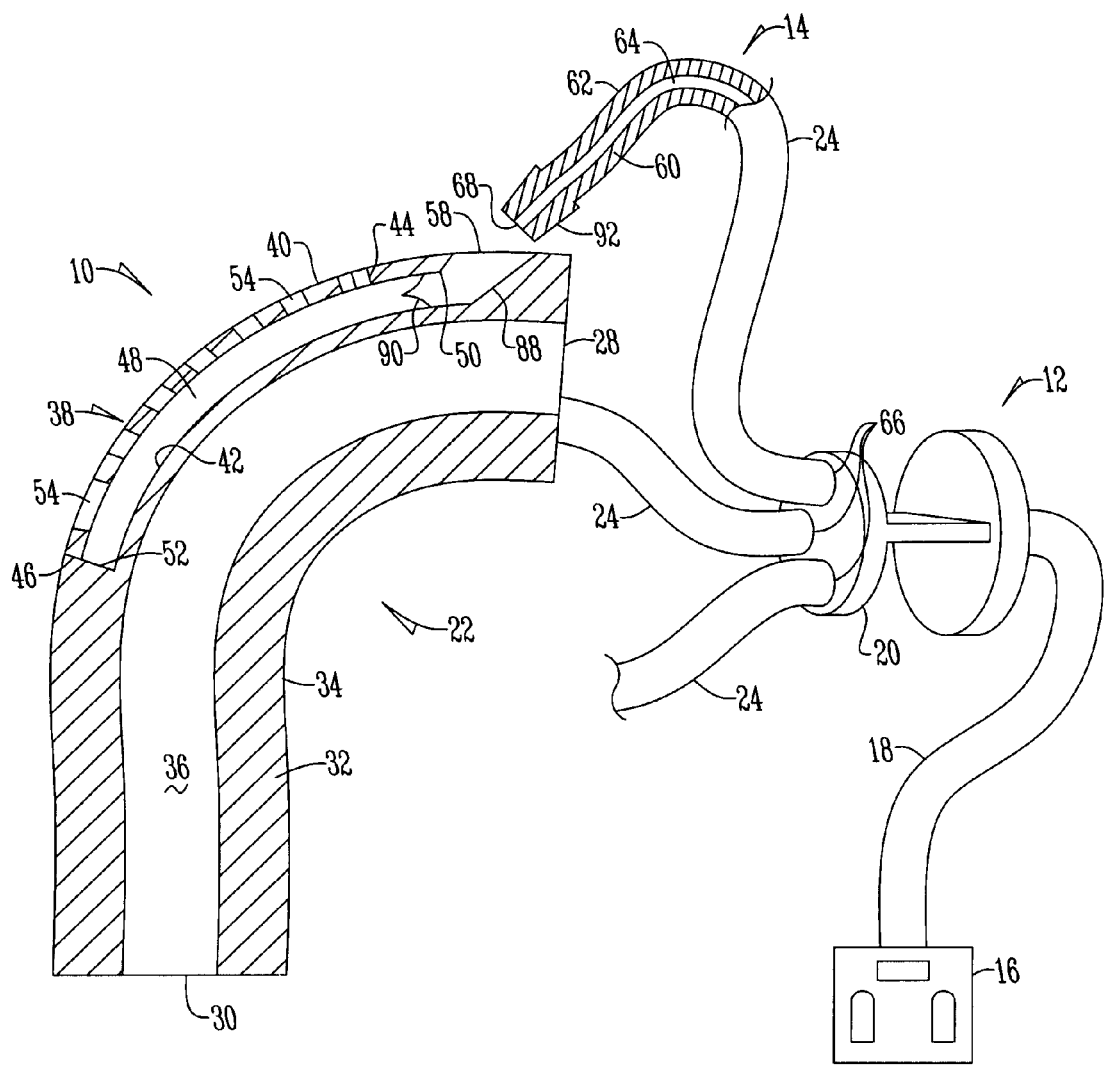
FIG. 1 is a perspective view in partial cross section of an embodiment of the present apparatus and system for administering medication.
Figure 2:
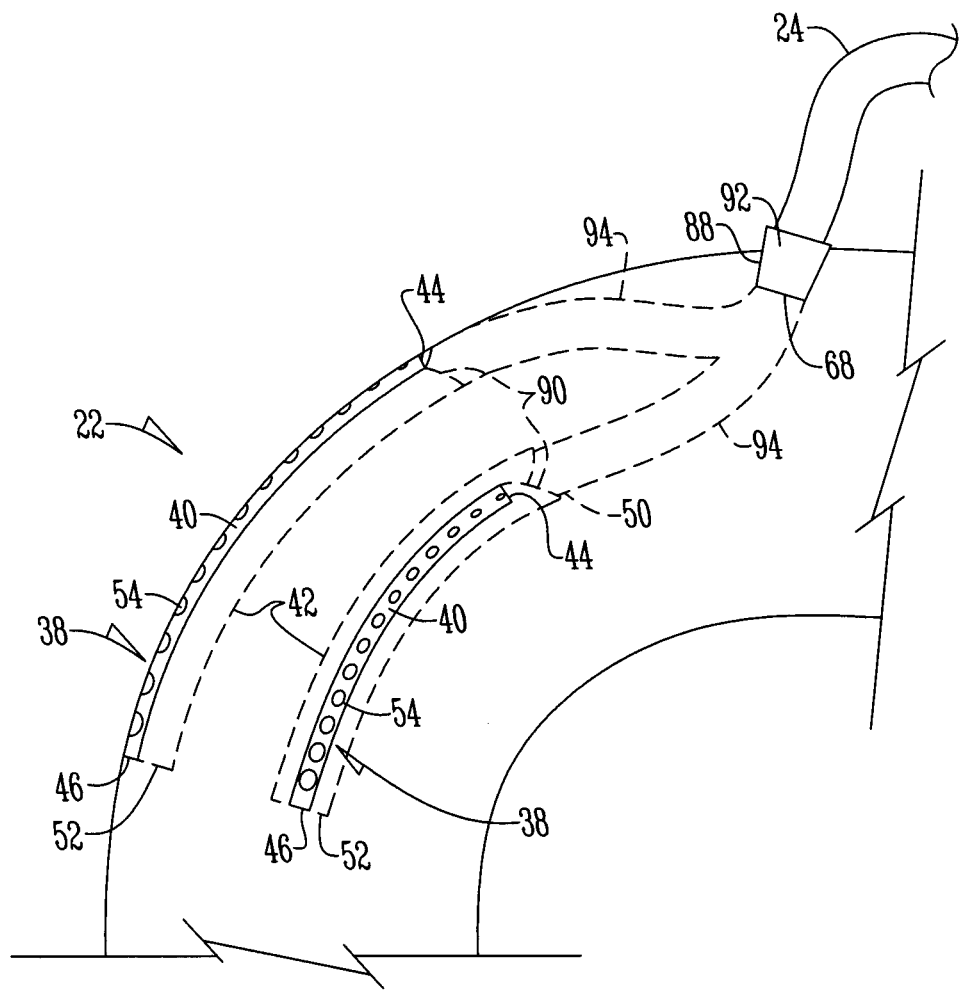
FIG. 2 is a perspective partial view of an embodiment of the present apparatus and system for administering medication.
Figure 3:
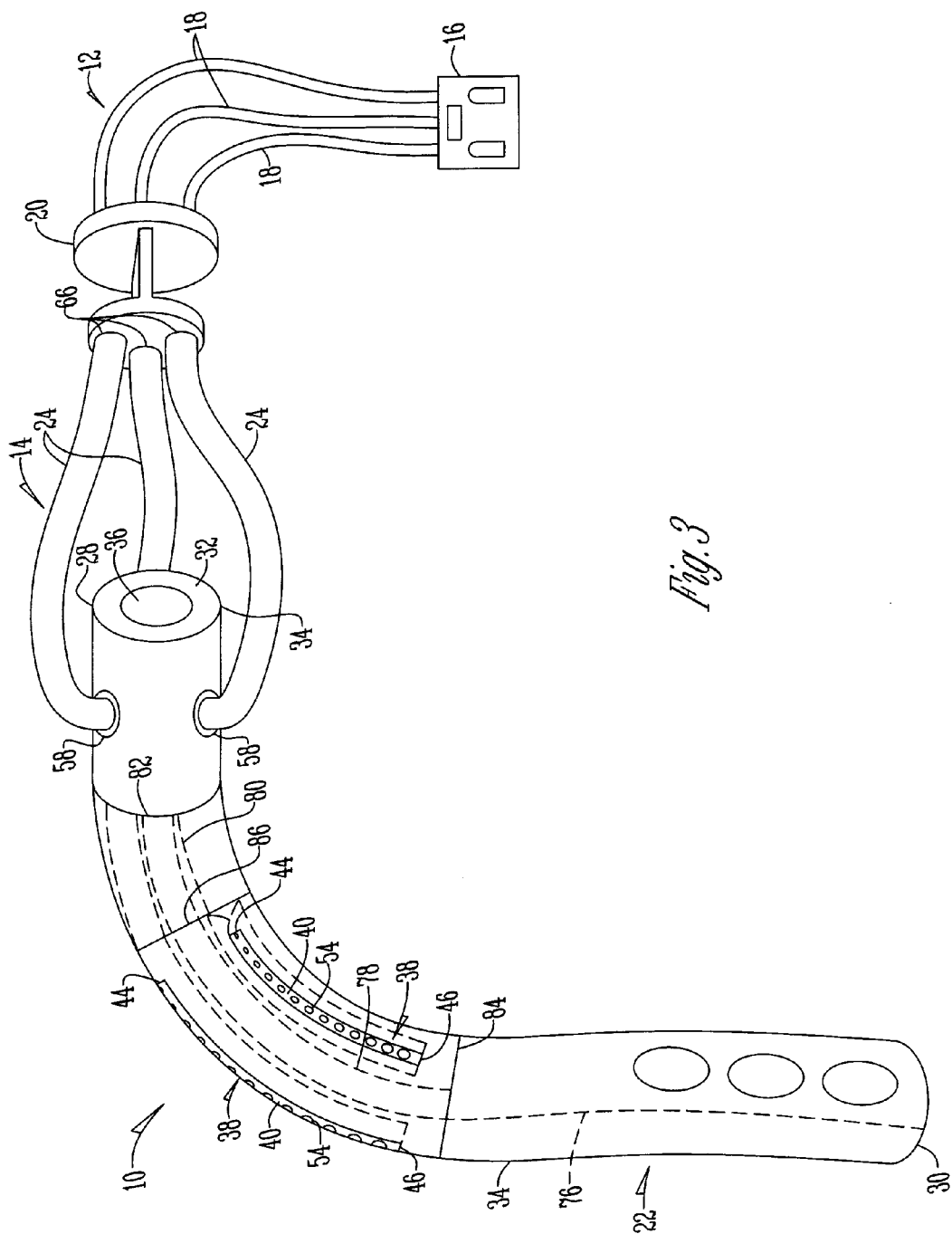
FIG. 3 is a perspective partial view of an embodiment of the present apparatus and system for administering medication.
Figure 4:
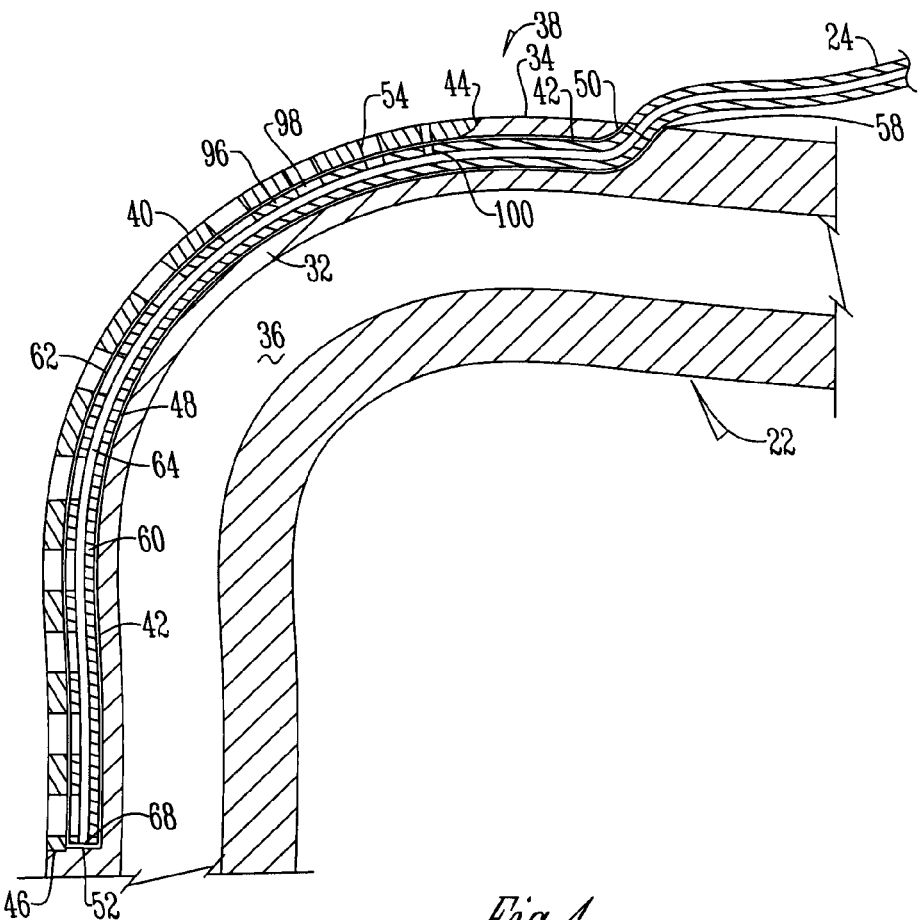
FIG. 4 is a side cross sectional view of another embodiment of the present apparatus and system for administering medication.
Figure 5:
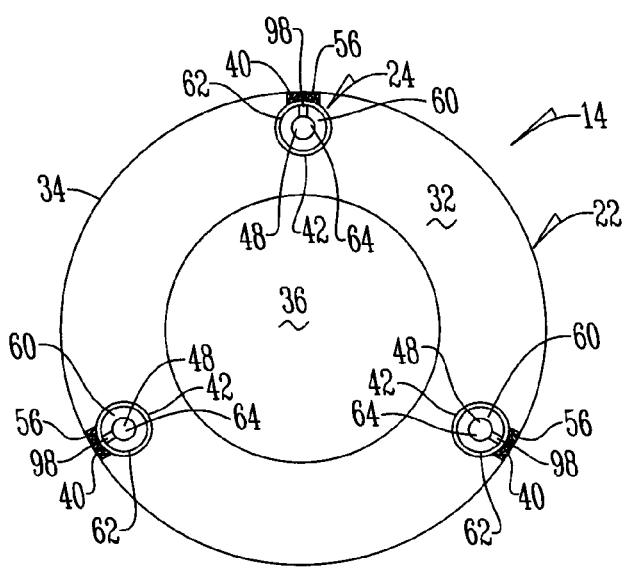
FIG. 5 is a front cross-sectional view of a treatment tube/catheter' medication administration section and a medication delivery conduit disposed therein of the present apparatus and system for administering medication.
Figure 6:
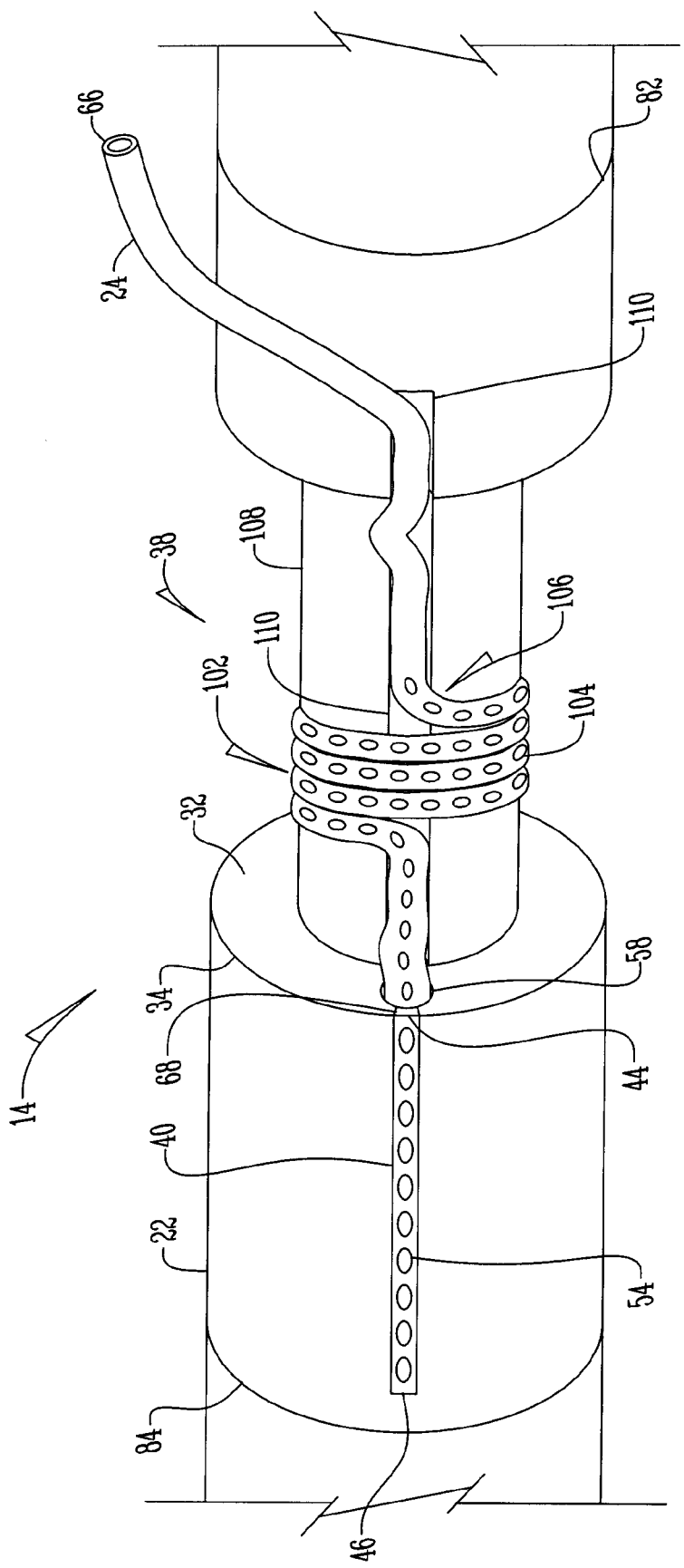
FIG. 6 is a perspective view of another embodiment of the treatment tube/catheter assembly of the present apparatus and system for administering medication.
Figure 7:
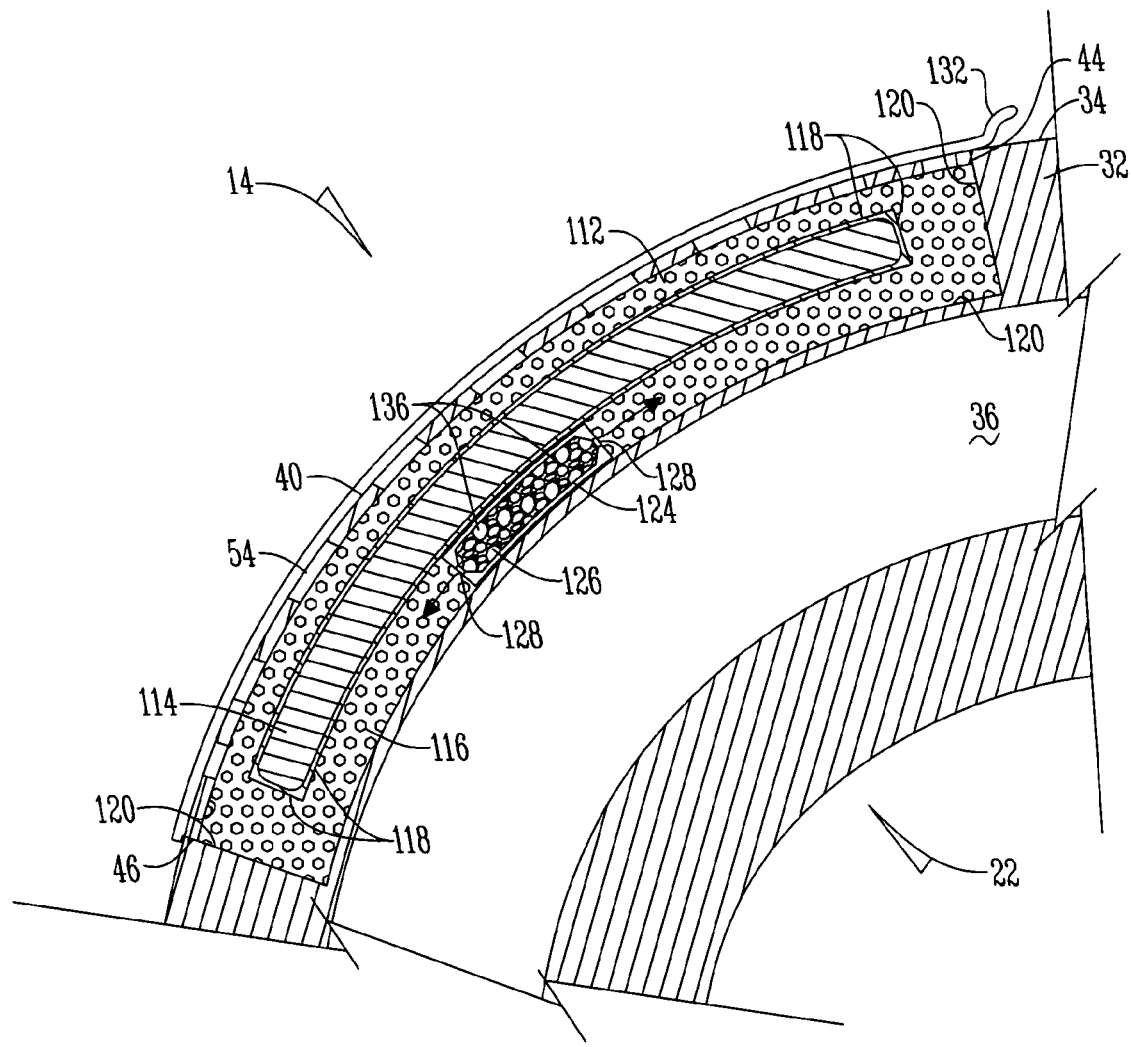
FIG. 7 is a side cross-sectional view of another embodiment of the present apparatus and system for administering medication.
Figure 8:
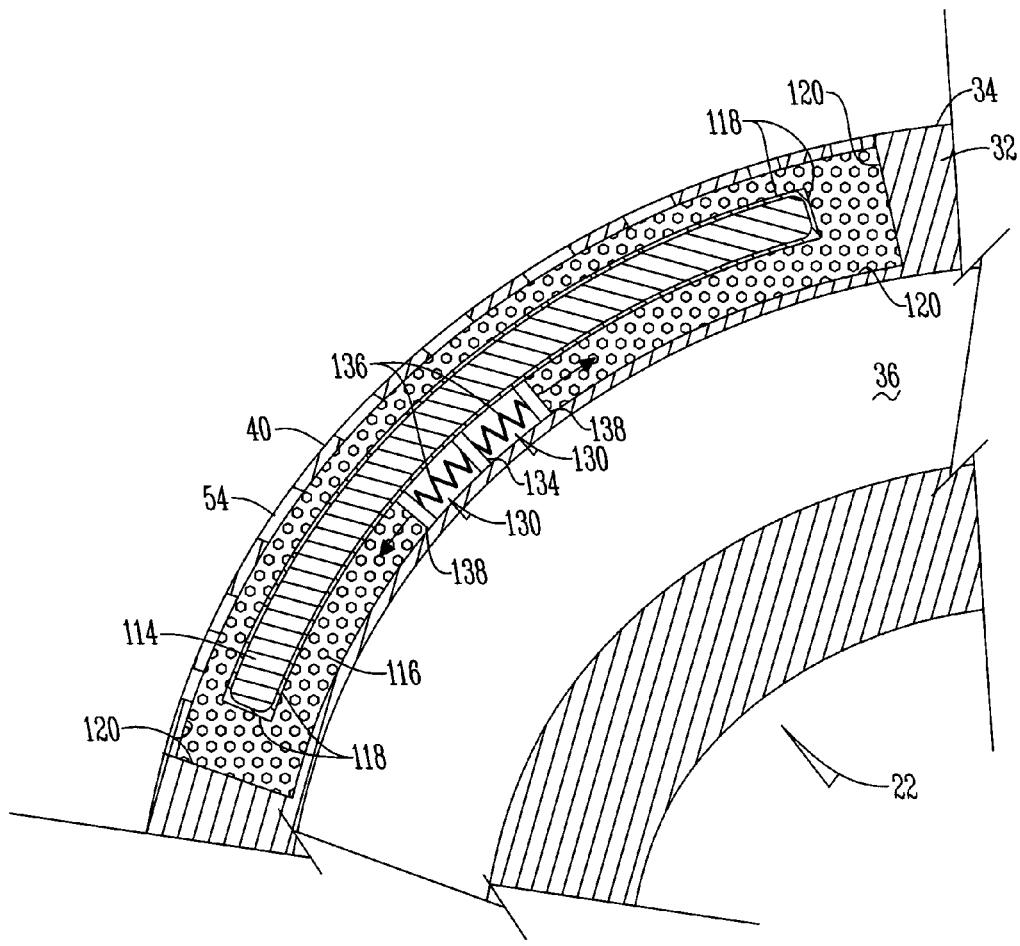
FIG. 8 is a side cross-sectional view of an alternate embodiment of the present apparatus and system for administering medication.
Figure 9:
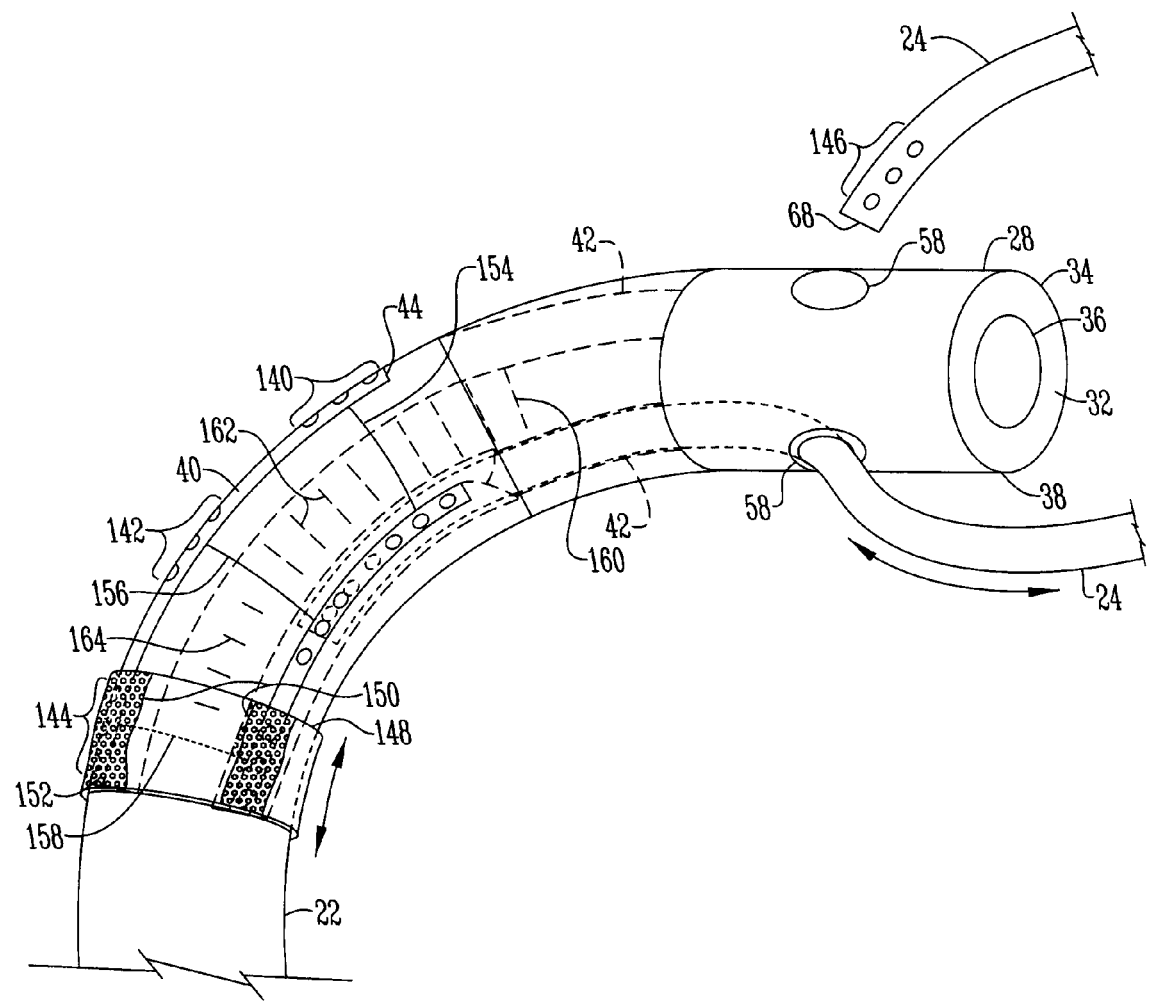
FIG. 9 is a perspective view of yet another embodiment of the treatment tube/catheter assembly of the present apparatus and system for administering medication.

Referring to the figures, an apparatus and system for administering medication 10 includes a medication delivery system 12 and a treatment tube/catheter assembly 14. The medication delivery system 12 can be embodied as a system as disclosed in U.S. Pat. No. 6,802,823 and can include a medication pump 16 such as an infusion pump, at least one connecting conduit 18 and an attachment hub 20. The one or more connecting conduits 18 are embodied as a tube or catheter in fluid communication with pump 16 and attachment hub 20, as the one or more connecting conduits 20 are attached at a first end to the pump 16 and the second end of each of the one or more conduits 16 is attached to the attachment hub 20 to deliver medication to the treatment tube/ catheter assembly 14. In one embodiment, one connecting conduit 18 is provided. Alternatively, a plurality of connecting conduits 18 are provided to deliver medication to each of the medication delivery conduits of the treatment tube/catheter assembly 14, as described below.

In a preferred embodiment, the medication delivered to the treatment tube/catheter assembly is anesthesia or numbing agent, preferably marcaine due to its ability to provide effective, long acting, and sustained anesthetic effects (as disclosed by http://www.druglib.com/druginfo/marcaine/descripton_pharmacology/), particularly in the mucous membranes of the pharynx, pleural tissue, and urethra, thereby dulling or substantially alleviating perceived pain in mucous membranes and pain sensitive tissues. Alternatively, the medication is any other appropriate local anesthetic suitable for interacting administratively and alleviating pain in the mucous membranes and pain sensitive tissues of internal body cavities, such as lidocaine.

The treatment tube/catheter assembly 14 includes a treatment tube/catheter 22 and a medication delivery conduit 24. The treatment tube/catheter 22 is any tube or catheter introduced into a patient's body to perform a variety of intubation functions including but not limited to cavity drainage, the administration of medication, nutrients, food, activated charcoal, and the like. In one embodiment, treatment tube/catheter 22 is a nasogastric tube. Alternatively, the treatment tube/catheter 22 is a Foley catheter, chest tube, or any of the various cavity drains such as an abdominal drain.

The treatment tube/catheter 22 in a preferred embodiment is a hollow, cylindrical tube extending from a first/proximal end 28 to a second/distal end 30 having a treatment tube/catheter wall 32. The treatment tube/catheter wall 32 has a central lumen 36 and an exterior surface 34. The wall 32 of the treatment tube/catheter 22 also includes a medication administration section 38. The medication administration section 38 includes one or more medication diffusion segments 40 extending axially along the exterior surface 34 of the treatment tube/catheter wall 32 and a corresponding number of one or more hollow tubular channels 42.

Each medication diffusion segment 40 is comprised of a section of the treatment tube/catheter's 22 body and has a first/proximal end 44 which is distal to the first/proximal end 28 of the treatment tube/catheter 22 and a second/distal end 46 which is proximal to the treatment tube/catheter's second/distal end 30. The length of the medication administration section 38 and correspondingly each of the one or more medication diffusion segments 40 is equivalent to the length of a patient's pain-sensitive tissues or membranes. Furthermore, each of the one or more medication diffusion segments 40 is positioned along the treatment tube/catheter's 22 body to correspond with the position at which such pain-sensitive tissues are engaged and contacted by the treatment tube/catheter 22, with the proximal and distal ends 44, 46 corresponding with the proximal and distal ends of such tissues such that the length of the medication administration section 38 and each medication diffusion segment 40 is adjacently aligned with the patient's pain-sensitive tissues. In one embodiment, the axial length and position of the medication administration section 38 and each medication diffusion segment 40 corresponds to and aligns with the pain sensitive tissues of the mucus membranes along the oral pharynx. Alternatively, the axial length and position of medication administration section 38 and each medication diffusion segment 40 corresponds to and aligns with the pain sensitive tissues along the pleural tissue, peritoneum, or, alternatively the urethra. Furthermore, each of the one or more medication diffusion segments 40 extends radially within the treatment tube/catheter 22 from the exterior surface 34 of the wall 32 to a hollow tubular channel 42.

Each of the one or more hollow tubular channels 42 are formed within the wall 32 of the treatment tube/catheter 22 adjacent the wall's exterior surface 34 to define a lumen 48 for each channel 42 which extends axially within the interior of the treatment tube/catheter's 22 wall 32 from a first/proximal end 50 to a second/distal end 52. Furthermore, each of the one or more hollow tubular channels 42 is disposed within the treatment tube/catheter's 22 wall 32 adjacent each of the one or more complimentary medication diffusion segments 40 which are formed within the exterior surface 34 of the treatment tube/catheter's 22 wall 32. The distal end 52 of each hollow tubular channel 42 is aligned with the distal end 46 of a complimentary medication diffusion segment 40 and, in one embodiment, the proximal end 50 of each hollow tubular channel 42 extends radially within the interior of the treatment tube/catheter wall 32 proximally beyond the proximal end 44 of the corresponding medication diffusion segment 40 and ports to the exterior surface 34 of the treatment tube wall 32 via an insertion opening 58.

In one embodiment, each medication diffusion segment 40 is comprised of a series of apertures 54 formed as openings or ports disposed within the treatment tube/catheter's 22 wall wherein each aperture 54 extends radially from the wall's exterior surface 34 to the lumen 48 of a corresponding hollow tubular channel 42. The apertures 54 permit fluid communication between the lumen 48 of each hollow tubular channel 42 and the exterior surface 34 of the tube/catheter's wall 32 such that medication introduced into each hollow tubular channel 42 is fluidly communicated and delivered from the lumen 48 of the channel 42 to the exterior surface 34 of the treatment tube 22 along each medication diffusion segment 40 of the medication administration section 38 via the apertures 50. In a preferred embodiment, the diameter of each successive aperture 54 increases gradually from the first proximal end 44 to the second distal end 46 of each of the medication diffusion segments 40 such that each successive aperture 54 has a diameter that is slightly larger than the adjacent aperture 54 proximal thereto. In one embodiment, the diameter of the apertures 54 ranges from 0.5-2 millimeters.

Alternatively, each medication diffusion segment 40 is comprised of a micropourous dispensing lattice 56. Each microporous dispensing lattice 52 is a segment of the treatment tube/catheter's 22 body having a network of micropores formed in the treatment tube/catheter's wall 32 extending from the wall's exterior surface 34 to the lumen 48 of the hollow tubular channel 42 such that medication introduced into the hollow tubular channels 42 is fluidly communicated and delivered to the exterior surface 34 of the treatment tube 22 along each of the medication diffusion segments 40 via the microporous dispensing lattice 56.

In a preferred embodiment, a series of three hollow tubular channels 42 are equidistantly spaced around the circumference of the treatment tube/catheter 22 within the catheter's wall 32 adjacent to a corresponding three complimentary medication diffusion segments 40 disposed through the exterior surface 34 of the treatment tube 22. Alternatively, the treatment tube/catheter 22 includes one or alternatively two hollow tubular channels 42 and a complimentary one or two medication diffusion segments 40 are provided in the wall 32 of the treatment tube/catheter 22. In yet another alternative embodiment, more than three hollow tubular channels 42 and medication diffusion segments 40 are provided.

The treatment tube/catheter assembly 14 also includes at least one medication delivery conduit 24. Each medication delivery conduit 24 is a hollow, cylindrical tube including a conduit wall 60 with an exterior surface 62 and a central lumen 64 which extends from a first/proximal end 66 to a second/distal end 68. The proximal end 66 of each of the one or more medication delivery conduits 24 is attached to the connecting hub 20. In one embodiment, the hub 20 channels medication from a single connecting conduit 18 attached to one end of the hub 20 to each of the one or more medication delivery conduits 24 attached to the opposite end of the hub 20 such that an equal volume of medication is permitted to flow at an equivalent, constant rate from the medication delivery source 12 via the pump 16 through the connecting conduit 18 and hub 20 into the lumen 64 of each of the one or more medication delivery conduits 24. Alternatively, the connecting hub 20 connects each of the one or more medication delivery conduits 24 to a single, complimentary connecting conduit 18 for each of the one or more medication delivery conduits 24 such that an equal volume of medication is permitted to flow at an equivalent, constant rate from the medication delivery source 12 via the pump 16 through the connecting conduit 18 and hub 20 into the lumen 68 of each medication delivery conduit 24.

Furthermore, in a preferred embodiment the treatment tube/catheter assembly 14 includes a first, second, and third set of printed indicia 76, 78, 80 comprised of length measurement markings, which in one embodiment is metric markings, such as centimeters and/or millimeters, or alternatively is English measurement markings such as inches or any other known means of marking length, provided along the exterior surface 34 of the treatment tube/catheter 22. The first set of printed indicia 76 is comprised of length measurement markings which extend between and indicate the distance from the distal end 30 of the treatment tube/catheter 22 to a first indicator mark 82 placed on the exterior surface 34 of the treatment tube/catheter 22 adjacent and distal to the treatment tube/catheter's proximal end 28 corresponding to the segment of the treatment tube/catheter 22 which is positioned at the opening of the body cavity, such as the nare or nasal opening or meatus, when a patient is fully intubated and being treated by the treatment tube/catheter 22. This provides the proper placement and position at which the distal end 30 of the treatment tube/catheter 22 is placed into a patient's body.

The second set of printed indicia 78 is comprised of a second set of length markings beginning at a second indicator mark 84 placed on the exterior surface 34 of the treatment tube/catheter 22 adjacent the distal end 46 of the medication administration section 38. The second set of printed indicia 78 extends between and indicates the length from the second indicator mark 80 to the first indicator mark 78. Finally, the third set of printed indicia 80 is comprised of a third set of length markings beginning at a third indicator mark 86 placed on the exterior surface 34 of the treatment tube/catheter 22 adjacent the proximal end 44 of the medication administration section 38, extending between and indicating the length from the third indicator mark 86 to the first indicator mark 82. The first, second and third sets of printed indicia 76, 78, 80 and corresponding first, second, and third indicator marks 82, 84, 86 thus provide the length of the treatment tube/catheter 22 inserted into a patient's body cavity and indicates the length from the body cavity opening to the pain-sensitive tissues. This thus provides for proper placement of the treatment tube/catheter 22 into the body cavity and alignment of the medication administration section 38 with the pain sensitive tissues during intubation.

In a first embodiment of the apparatus and system for administering medication 10, each of the one or more hollow tubular channels 42 includes a corresponding insertion port 88 extending within the treatment tube/catheter wall 32 from the insertion opening 58 associated with each hollow tubular channel 52 to the proximal end 50 of each hollow tubular channel 42. Each port 88 has a tubular cross-section, and in a preferred embodiment, each port 88 has the profile of a funnel or cone with a diameter that decreases as the port 88 extends from the insertion opening 58 into the treatment tube/catheter wall 32 to the proximal end 50 of an associated hollow tubular channel 42. Additionally, a one way valve 90 is provided within each hollow tubular channel 42 adjacent each channel's proximal end 50 beyond the distal end of each insertion port 88. The one way valve 90 permits medication to be introduced and delivered into the interior of the treatment tube/catheter's wall 32 to each of the one or more hollow tubular channels 42 while at the same time ensuring that no medication, air, fluids, or the like are able to escape outward from the interior of the patient's body cavity through the one or more hollow tubular channels 42 and compromise the internal and external pressure differential of a patient's body cavities during intubation procedures.

Furthermore, one or more medication delivery conduits 24 are provided for each of the one or more hollow tubular channels 42 and associated medication diffusion segments 40. The second/distal end 68 of each of the one or more medication delivery conduits 24 includes a connecting adaptor 92 which is received by any one of the plurality of the insertion ports 88 through which the lumen 64 of the conduit 24 extends. The connecting adaptor 92 preferably is a hollow plug with an outer, conical profile which matingly aligns with that of the insertion port 88, such that upon insertion, the connecting adaptor 92 is snugly secured within the complimentary profile of the insertion port 88. The outer profile of the connecting adaptor 92, upon insertion into an insertion port 88, permits the fluid communication and delivery of medication flowing out through the distal end 68 of each of the one or more medication delivery conduits 24 through each one way valve 90 and into each of the one or more corresponding hollow tubular channels 42.

In an alternative version of this embodiment, only one medication delivery conduit 24/connecting adaptor 92 and associated insertion port 88 are provided to deliver medication to a plurality of two or more hollow tubular channels 42 within the interior of the treatment tube/catheter's wall 32 adjacent a plurality of two or more corresponding medication diffusion segments 40. In this embodiment, each of the two or more hollow tubular channels 42 includes an intermediate channel 94 extending within the interior of the treatment tube/catheter's wall 32 from the proximal end 50 of each hollow tubular channel 42 to the insertion port 88. Thus, once the connecting adaptor 92 is secured within the insertion port 88, medication provided by a single medication delivery conduit 24 disposed within a single insertion port 88 is fluidly communicated through the interior of the treatment tube/catheter's wall 32 via the intermediate channels 94 to each of the one or more hollow tubular channels 42 and administered to a patient's pain sensitive tissues and membranes adjacent the one or more medication diffusion segments 40. In this embodiment, additional tubing is eliminated and by utilizing a connecting adaptor 92 of a single medication delivery conduit 24 inserted within a single insertion port 88, upon attachment of the connecting adaptor 92 within the insertion port 88, medication is ready to be delivered to the treatment tube/catheter assembly 14 more quickly and easily.

In operation, the proximal ends 66 of each of the one or more medication delivery conduits 24 are attached to the complimentary attachments on the second end of the attachment hub 20 such that each of the one or more medication delivery conduits 24 is in fluid communication with the one, or alternatively, one or more complementary medication delivery conduits 18 via the attachment hub 20. Each of the one or more connecting conduits 18 is attached in fluid communication with the medication pump 16 and a source of medication (not shown) such that pump 16 fluidly supplies the conduits 18 with liquid medication.

With the first/proximal ends 66 of each of the one or more medication delivery conduits 24 attached to the hub 20, the distal ends 68 of each of the one or more medication delivery conduits 24 are attached to the treatment tube/catheter 22 to deliver liquid medication into each complimentary hollow tubular channel 42 by inserting each connecting adaptor 92 at the second/distal end 68 of each individual medication delivery conduit 24 through each channel's insertion opening 58 and into each complimentary insertion port 88, until the second/distal end 68 of each medication delivery conduit 24 reaches and is positioned adjacent to the first/proximal end 50 of the complimentary hollow tubular channel 42 and the conical outer profile of the connecting adaptor 92 is snugly and securely disposed within the complimentary conical profile of the insertion port 88.

Next, or alternatively, prior to attaching the distal ends 68 of each of the one or more medication delivery conduits 24 to the treatment tube/catheter 22, the treatment tube/catheter assembly 14 is inserted into a patient's body. The first set of printed indicia's 76 length measurement markings are utilized to determine the progressive distance at which the distal end 30 of the treatment tube/catheter 22 is being inserted into the patient's body cavity to ensure the proper placement, depth, and position of the insertion of the distal end 30 of the treatment tube/catheter 22. The first indicator mark 82 designates the boundary point of the treatment tube/catheter's 22 body which lies adjacent to and aligns with the opening of a patient's body cavity when the patient is fully intubated. At the same time, the second and third sets of printed indicia 78, 80, along with the second and third indicator marks, 84, 86 are utilized to determine the progressive distance at which the medication administration section 38 is being inserted into the patient's body cavity with respect to the first indicator mark 82. This ensures the treatment tube/catheter's 22 medication administration section 38 is properly placed and positioned to be aligned adjacent deliver pain medication to the patient's pain sensitive tissues when the patient is fully intubated. Therefore, the second indicator mark 84 and distal end 46, and third indicator mark 86 and proximal end 44 of the treatment tube/catheter's 22 medication administration section 38 aligns with the distal and proximal ends of the patient's pain sensitive tissues, respectively.

Upon activation of the pump 16, liquid medication is pumped from the source of medication (not shown) through the one or more connecting conduits 18 and the attachment hub 20 and into each of the one or more medication delivery conduits 24 such that an equal amount of liquid medication is delivered at a constant, consistent rate into each of the one or more medication delivery conduits 24 and flows through the lumen 64 of the conduits 24 from the proximal 66 to the distal end 68. With the connecting adaptors 92 of the second/distal ends 68 of each medication delivery conduit 24 snugly and securely received within each insertion port 88 adjacent to and in fluid communication with the proximal end 50 of each hollow tubular channel 42, an equal amount of liquid medication is pumped at a constant rate from the medication delivery conduits 24 into each hollow tubular channel 42 through the connecting adaptors 92 and the one way valves 90, and the lumen 48 of each channel 42 begins to fill with medication as liquid medication flows into each hollow tubular channel 42 from the proximal end 50 of each channel 42 to the second/distal end 52.

As the lumen 48 of each channel 42 begins to fill with medication, the pumped liquid medication progressively flows through the wall 32 to the exterior surface 34 of the treatment tube/catheter 22 along each medication diffusion segment 40 of the medication administration segment 38 via the apertures 54 which increase in diameter from the first proximal end 44 to the second distal end 46 of the medication diffusion segments 40. Specifically, the liquid medication first encounters and flows through the smaller apertures 54 at the proximal end 44 before reaching the progressively larger apertures 54 at the distal end 46 of the medication diffusion segments 40. This thereby restricts the flow of liquid medication through the smaller apertures 54 at the proximal end 44 of the medication diffusion segments 40 and ensures that the liquid medication is pushed by virtue of the pump to the second/distal end 46 of the medication diffusion segments 40, wherein the gradually increasing diameters of the apertures 54 from the proximal end 44 to the distal end 46 of the medication diffusion segments 40 prevent the majority of liquid medication from being dispensed through the apertures 54 at the proximal end 44 of the medication diffusion segments 40. The gradually increasing diameters of the apertures 54 also provide a consistent, continuous, and controlled delivery of liquid medication being dispensed from the hollow tubular channels 42, through each medication diffusion segment 40 to the adjacent pain sensitive membranes and tissues in contact with the treatment tube/catheter 22.

Alternatively, as the lumen 48 of each channel 42 begins to fill with medication, the pumped liquid medication flows through the wall 32 to the exterior surface 34 of the treatment tube/catheter 22 and the patient's pain-sensitive tissues and membranes adjacent each medication diffusion segment 40 of the medication administration segment 38 via the microporous dispensing lattice 56. The micropores of the microporous dispensing lattice 56 of each medication diffusion segment 40 fluidly communicate the medication through the wall 32 to the exterior surface 34 along the length of the medication administration section 38 to provide a controlled outflow and delivery of pain medication directly to the pain sensitive membranes and tissues contacting the treatment tube/catheter 22 along the entire length of such tissues from the first/proximal end 44 to the second/distal end of the medication administration section 38.

In addition, by delivering pain medication from a plurality of three or more medication delivery conduits 24 to a corresponding plurality of three or more medication dispensing diffusion segments 40 which provide a matrix of diffusion segments positioned around the circumference of the treatment tube/catheter wall's 32 exterior surface 34, anesthesia is delivered from the three or more sides of the medication administration section 38 to the surrounding, adjacent pain-sensitive mucous membranes and tissues. This creates a halo of anesthesia around the entire radial circumference of the treatment tube/catheter's exterior surface 34 and surrounding tissues to supply a continuous, controlled, and consistent flow of pain medication to the tissues. This provides a greater degree of contact between the dispensed medication or anesthesia pain sensitive tissues surrounding the treatment tube/catheter 22 and more effective control of pain. Furthermore, by providing each of the one or more medication delivery conduits 24 within a hollow tubular channel 42 disposed within the wall 32 of the treatment tube/catheter 22, the surface area of the treatment tube/catheter 22 and treatment tube/catheter assembly 14 in contact with the pain sensitive mucous membranes and tissues is decreased. This further ameliorates the pain involved in catheterization or intubation, as the more surface area of a treatment tube or catheter in contact with such tissues and membranes the more pain or discomfort is experienced by the patient.

In a second embodiment of the apparatus and system for administering medication 10, the connecting adaptor 92 of the second/distal end 68 is eliminated, and the second/distal end of each medication delivery conduit 24 includes a medication delivery segment 96 comprised of a single, linear series of apertures 98 in the conduit wall 60 beginning at a proximal end 100 which is distal to the proximal end 66 of the conduit 24 and terminating at the distal end 68 of the conduit 24. The apertures 98 of the medication delivery segment 96 are formed as openings or ports extending through the conduit wall 60 from the central lumen 64 and the exterior surface 62 such that medication introduced into the central lumen 64 fluidly passes through the conduit wall 60. In a preferred embodiment, the diameter of each successive aperture 98 increases gradually from the proximal end 100 of the medication delivery segment 96 to the distal end 68 of the medication delivery segment 96 and medication delivery conduit 24 such that each successive aperture 98 has a diameter that is slightly larger than the adjacent aperture 98 proximal thereto. In one embodiment, the diameter of the apertures 72 ranges from 0.5-2 millimeters.

The outer diameter of each medication delivery conduit 24 is sized to correspond and matingly align with the diameter of each of the treatment tube/catheter's 24 hollow tubular channels 42 and insertion openings 58 such that all or alternatively a portion of each conduit's 24 medication delivery segment 96 is passed through the treatment tube's 22 insertion opening 58 and inserted into the treatment tube's 22 hollow tubular channels 42 such that the conduit's 24 medication delivery segment 96 is securely and snugly housed within the treatment tube/catheter's 22 hollow tubular channels 42.

In a preferred embodiment, one medication delivery conduit 24 is provided for each of the one or more hollow tubular channels 42 such that a medication delivery conduit 24 is inserted into each of the one or more tubular channels 42 to supply each of the corresponding one or more medication diffusion segments 40 with a constant flow of medication. In one embodiment, the length of each conduit's 24 medication delivery segment 96 is equivalent to that of each of the treatment tube's 22 medication diffusion segments 40, wherein the entire length of each medication delivery segment 96 is disposed within each hollow tubular channel 42 such that the proximal end 100 of the medication delivery segment 96 is aligned with the proximal end 44 of a complimentary medication diffusion segment 40 and the distal end 68 of each conduit 24 is positioned at the distal end 52 within each hollow tubular channel 42 and is aligned adjacent to the distal end 46 of each corresponding medication diffusion segment 40.

In an embodiment wherein the treatment tube/catheter's 22 medication diffusion segments 40 are comprised of a series of apertures 54, the apertures 98 of the delivery conduit's 24 medication delivery segment 96 have a diameter and spacing equal to and corresponding with that of each of the medication diffusion segment's 40 apertures 54. Specifically, the size and spacing of the apertures 98 correspond with those of the apertures 54 such that when the medication delivery segment 96 of a medication delivery conduit 24 is inserted within a treatment tube/catheter's hollow tubular channel 42 adjacent a medication diffusion segment 40, the apertures 98 correspond to and align with the apertures 54 of a medication diffusion segment 40 opening into the lumen 48 each hollow tubular channel 42, and preferably, each aperture 98 has a diameter of equal size to the particular aperture 54 of a medication diffusion segment 40 with which the conduit's aperture 98 aligns. In this embodiment, the apertures 98, 54 of the conduit and tube/catheter's medication segments 96, 40, respectively, align and have correspondingly gradually increasing diameters from their proximal ends 100, 44 to their distal ends, 68, 46, respectively. Thus, medication flowing through the central lumen 64 of the medication delivery conduit 24 is delivered through the apertures 98 and the conduit wall 60 and the correspondingly aligned apertures 54 of each medication diffusion segment 40 to the exterior surface 34 of the treatment tube/catheter 22 along the medication administration section 38. Alternatively, the apertures 98 of each of the one or more medication delivery conduits 24 interface with each of the one or more micropourous dispensing lattices 56 such that medication flowing through the central lumen 64 of the medication delivery conduit 24 is delivered through the apertures 98 of the conduit wall 60 and the network of micropores 56 of each of the medication diffusion segments 40 to the exterior surface 34 of the treatment tube/catheter 22 along the medication administration section 38.

Notwithstanding, in either embodiment, the apertures 98 of each of the one or more medication delivery conduits 24 preferably have gradually increasing diameters from the proximal end 100 to the distal end 68 of each of the delivery segments 96 to provide a constant outflow and delivery of liquid medication or anesthesia to the medication diffusion segments 40 such that liquid medication or anesthesia is gradually dispensed through the apertures 98 while at the same time being pumped to the distal end 68 and filling the medication delivery conduit 24 to provide a consistent flow and controlled delivery of liquid medication. This ensures that medication is delivered evenly along the length of the medication administration section's segments 40 from their proximal to their distal ends 44, 46. In this manner, the increasing diameters of the apertures 98 prevent the majority of liquid anesthetic or medication from being delivered to the proximal, leading portions 44 of the medication diffusion segments 40, ensuring that anesthetic is dispensed along the entire length of the pain sensitive tissues.

In operation of this embodiment of the invention, the distal ends 68 of each of the one or more medication delivery conduits 24 are inserted through the insertion openings 58 on the exterior surface 34 of the treatment tube/catheter's wall 32 and into each of the one or more complimentary hollow tubular channels 42. The distal ends 68 of each medication delivery conduit 24 reaches and aligns with the distal ends 46 of each hollow tubular channels 42 and the proximal ends 100 of the conduit's 24 medication delivery segment 96 aligns with the proximal ends 44 of the medication diffusion segments 40. Thus, the entire length of each conduit's 24 medication delivery segment 96 is disposed within each hollow tubular channel 42 within the wall 32 of the treatment tube/catheter 22 with a leading portion and the proximal ends 66 of each medication delivery conduit 24 extending proximally out of the insertion openings 58 to the exterior surface 34 of the treatment tube/catheter's wall 32 for attachment to the hub 20. As each conduit's 24 medication delivery segment 96 is inserted into one of the plurality of tubular channels 42, the apertures 98 of the medication delivery segment 96 are oriented outward toward the exterior surface 34 of the treatment tube/catheter wall 32 such that the apertures 98 of each conduit's 24 medication delivery segment 96 are positioned adjacent to and facing each medication diffusion segment 40 such that the apertures 98 align with the apertures 54. In an alternative embodiment the apertures 98 open into the microporous dispensing lattice 56 of each medication diffusion segment 40.

Next, the treatment tube/catheter assembly 14 is inserted into a patient's body utilizing the first, second, and third sets of printed indicia 76, 78, 80 and indicator marks 82, 84, 86 to determine proper insertion, placement, and positioning of the treatment tube/catheter assembly 14 within the patient's body as described above.

The proximal ends 66 of each of the one or more medication delivery conduits 24 are then attached to the complimentary attachments on the second end of the attachment hub 20 which is attached in fluid communication to the one or more connecting conduits 18 each attached in fluid communication with the medication pump 16 and a source of medication (not shown) which fluidly supplies the conduits 18 with liquid medication. Each of the one or more medication delivery conduits 24 is attached in fluid communication with the one or more connecting conduits 18 via the attachment hub 20. Upon activation of the pump 16, an equal amount of liquid medication is supplied to each of the one or more medication delivery conduits 24, flowing into and filling the lumen 64 of each medication delivery conduit 24 with liquid medication from the proximal 66 to the distal end 68. Once the medication reaches the apertures 98 of the medication delivery segment 96 and begins to fill each conduit 24, the pumped medication begins to flow through the apertures 98 of the conduit wall 60 aligned adjacent to and in fluid communication with each medication diffusion section 40. Consequently, the medication flowing through the apertures 98 of the medication delivery segment 96 is passed through each conduit wall 60 and delivered to the corresponding apertures 54. Alternatively, once the pumped medication begins to flow through the apertures 98 of the conduit wall 60 aligned adjacent to and in fluid communication with each medication diffusion section 40, the micropores of the microporous dispensing lattice 56 of each medication diffusion segment 40 fluidly communicate the medication dispensed from the apertures 98 of the medication delivery segment 96 through the wall 32 to the exterior surface 34 along the length of the medication administration section 38 to provide a controlled outflow and delivery of pain medication directly to the pain sensitive membranes and tissues contacting the treatment tube/catheter 22 throughout the entire length of such tissues from the first/proximal end 44 to the second/distal end of the medication administration section 38.

Specifically, liquid medication is pumped from the proximal end of 66 of each medication delivery conduit 24 to the second/distal end 68 of each conduit 24 and the central lumen 64 of each medication delivery conduit 24 fills with medication. The pumped liquid medication progressively flows through the apertures 98 which increase in diameter from the first proximal end 100 to the second distal end 68 of the medication delivery segment 96, flowing first through the smaller apertures 98 at the proximal end 100 of the medication delivery segment 96. This thereby restricts the flow of liquid medication through the smaller apertures 98 at the proximal end 100 of the medication delivery segment 96 and ensures that the liquid medication is pushed by virtue of the pump to the second/distal end 68 of the medication delivery segment 96. Thus, the gradually increasing diameters of the apertures 98 from the proximal end 100 to the distal end 68 of the medication delivery segment 96 prevents the majority of liquid medication being dispensed through the apertures 98 at the proximal end 100 of the medication delivery segment 96. They also provide a consistent, continuous, and controlled delivery of liquid medication being dispensed from the medication delivery segment 96, through each medication diffusion segment 40 to the adjacent pain sensitive membranes and tissues in contact with the treatment tube/catheter 22.

In addition, as provided above, by delivering pain medication from a plurality of three or more medication delivery conduits 24 to a corresponding plurality of three or more medication dispensing diffusion segments 40 which provide a matrix of diffusion segments positioned around the circumference of the treatment tube/catheter wall's 32 exterior surface 34, anesthesia is delivered from the three or more sides of the medication administration section 38 to the surrounding, adjacent pain-sensitive mucous membranes and tissues. This creates a halo of anesthesia around the entire radial circumference of the treatment tube/catheter's exterior surface 34 and surrounding tissues to supply a continuous, controlled, and consistent flow of pain medication to the tissues. This provides a greater degree of contact between the dispensed medication or anesthesia pain sensitive tissues surrounding the treatment tube/catheter 22 and more effective control of pain. Furthermore, by providing each of the one or more medication delivery conduits 24 within a hollow tubular channel 42 disposed within the wall 32 of the treatment tube/catheter 22, the surface area of the treatment tube/catheter 22 and treatment tube/catheter assembly 14 in contact with the pain sensitive mucous membranes and tissues is decreased. This further ameliorates the pain involved in catheterization or intubation, as the more surface area of a treatment tube or catheter in contact with such tissues and membranes the more pain or discomfort is experienced by the patient.

In a third embodiment of the apparatus and system for administering medication 10 wherein the treatment tube/catheter 22 is embodied as a chest tube, the treatment tube/catheter assembly 14 is designed to not only deliver medicine such as local anesthetic to pain sensitive membranes of the pleural cavity via a medication diffusion segment 40 of the treatment tube/catheter 22 but also delivers a greater amount of medicine to the ribs and intercostal muscle layer directly and exclusively via an external medication delivery segment 102 of the medication delivery conduit 24. In this embodiment, only a single hollow tubular channel 42 and corresponding medication diffusion segment 40 are provided within the treatment tube's wall 32. Furthermore, only a single medication delivery conduit 24 is provided, and includes an external medication delivery segment 102. The external medication delivery segment 102 extends from a first/proximal end 106 which is distal to the first/proximal end 66 of the medication delivery conduit 24 to the second distal end 68 of the conduit 24 and includes a linear series of apertures 104 extending radially through the conduit wall 60 and permitting liquid medication to flow from the central lumen 64 of the conduit 24 to the exterior surface 62 along the length of the external medication delivery segment 102. The second/distal end 68 of the medication delivery conduit 24 and external medication delivery segment 102 includes a connecting adaptor 92 through which the central lumen 64 extends, and in a preferred embodiment, has a conical profile which mates with the complimentary conical profile of an insertion port 88 extending from the insertion opening 58 to the proximal end 50 of the hollow tubular channel 42. A one-way valve 90 is also provided within the hollow tubular channel 42 adjacent the channel's first/proximal end 50 distal with respect to the distal end of the insertion port 88.

The wall 32 of the treatment tube 22 includes a recessed segment 108 formed as an elongated radial groove or recess in the exterior surface 34 of the tube wall 32 adjacent and proximal to the proximal end of the medication diffusion segment 40. In a preferred embodiment, the length of the recessed segment 108 sized to correspond with, and preferably, be longer than the width of a patient's intercostal rib and muscle layer. Disposed within the outer surface of the recessed segment 108 is an axial groove 110 of a size that corresponds with the diameter of the exterior surface 62 of the medication delivery conduit 24 such that the medication delivery conduit 24 is received and secured, or "snapped," within the groove 110 to hold the conduit 24 in place and adjust the position of a leading, proximal end 106 of the external medication delivery segment 102 within the groove. Additionally, depending upon the requisite positioning and length of the external medication delivery segment 102 as determined by the position and length at which a patient's intercostal tissues engage the recessed segment 108 of the chest tube 22, the axial groove 110 holds the conduit's 24 external medication delivery segment 102 in place and adjusts the position of an end or a section of the external medication delivery segment 102 proximal to the distal end 68 of the medication delivery conduit 24 within the groove. In this manner, the medication delivery conduit's external medication delivery segment 102 is properly aligned and positioned to deliver medication along the width of a patient's pain-sensitive intercostal rib and muscle layer. The groove 110 is axially aligned with the hollow tubular channel 42 and the channel's 42 insertion opening 58 and insertion port 88 which are oriented to open into the distal end of the recessed segment 104 of the treatment tube's wall 36 adjacent the axial groove 106. Optionally, the axial groove 110 extends proximally beyond the recessed section 108 and is disposed within the exterior surface 34 of the treatment tube's wall 32 adjacent the proximal end of the recessed section 108.

Additionally, in the present embodiment, the length of the external medication delivery segment 102 is greater than that of the treatment tube's 22 medication administration section 38 and diffusion segment 40 and the hollow tubular channel 42. Thus, when the connecting adaptor 92 at the distal end 68 of the conduit 24 is inserted into the insertion port 88 and reaches the channel's distal end 46, the external medication delivery segment 102 and the proximal end 66 and a leading portion of the medication delivery conduit 24 proximal with respect to the external medication delivery segment 102 extends proximally from the hollow tubular channel's 42 insertion opening 58 into the recessed segment 108 of the treatment tube's wall 32.

In operation, the connecting adaptor 92 at the distal end 68 of the medication delivery conduit 24 is inserted through the treatment tube's insertion opening 58 and into the hollow tubular channel 42 until the connecting adaptor is snugly secured within the insertion port with the distal end of the connecting adaptor 92 adjacent and in fluid communication with the first/proximal end 50 of the hollow tubular channel 42. The proximal end 106 and the external medication delivery segment 102 extends proximally out of the hollow tubular channel 42 and medication diffusion segment 40 into the recessed segment 108 of the treatment tube's wall 32. Based upon the position of the chest tube 22 and the width of a particular patient's intercostal muscle and rib layer, the length and position of external medication delivery segment 102 is adjusted to deliver medicine to the patient's rib and muscle area via the apertures 104 at any width and position at which these tissues contact the recessed segment 108. In order to do so, all or a proximal portion of the medication delivery segment 102 is wrapped around the recessed segment 108 to account for and deliver pain medications to different lengths of intercostal walls engaging the recessed segment 108 at different positions. Furthermore, the width or distance of the external delivery segment 102 along the recessed segment 108 can be adjusted both by how tightly and also by how many times the external delivery segment 102 is wrapped around the circumference of the recessed segment 108.

Specifically, upon determining the width of a patient's muscle and rib layer in addition to the position the width of such tissues will occupy along the length of the recessed segment 108, the external medication delivery segment 102 is wrapped helically around the outer circumference of the recessed segment 108 such that the apertures 104 face radially outward to create a wrapped section of the external medication delivery segment 102 having a width which corresponds to the width of the patients intercostal rib and muscle layer at a position on the recessed segment 108 corresponding to the position at which the patients rib and muscle layer will contact the segment 102 and external medication delivery segment 102 once the patient is fully intubated.

Once the external medication delivery segment 102 is wrapped to provide the appropriate width at the appropriate position along the recessed segment 108, the proximal end 66 of the medication delivery segment 24 and the section of the conduit 24 proximal to the medication delivery segment 102 is received and secured, or "snapped," within the axial groove 110. This holds the conduit 24 in place to ensure that the width of the wrapped external medication delivery segment 102 is secured in the proper position within the recessed segment 108. Therefore, the medication is delivered to the entire width of the patient's rib and muscle area through which the chest tube 22 is inserted and engaging via the outwardly facing apertures 104 of the helically wrapped coils of the external medication delivery segment 102. At the same time this ensures that medication is administered exclusively adjacent the rib and muscle wall and within the pleural cavity. This also prevents the medicine from being delivered from the conduit proximal to the recessed segment 108 and chest tube 22 at the outside of the chest cavity wall. Furthermore, with the external delivery segment 102 wrapped around the entire radial circumference of the recessed segment 108 and directly contacting the intercostal wall and rib tissues, a greater amount of pain medication is delivered directly to these tissues from the apertures 104 throughout the entire radial circumference of the helically wrapped external delivery segment 102 to provide more direct, effective and comprehensive pain control, while at the same time delivering medication to the internal pain-sensitive tissues and membranes within the chest cavity adjacent the medication delivery segment 40 via the medication delivery conduit 24.

In a fourth embodiment of the apparatus and system for administering medication 10, the wall of the treatment tube/catheter 22 includes one or more hollow medication chambers 112 adjacent to each of the one or more medication diffusion segments 40. Each of the one or more hollow medication chambers 112 is a self-contained medication chamber which extends radially within the treatment tube/catheter wall 32 from the interior wall of the treatment tube/catheter 22 adjacent its central lumen 36 to each medication diffusion segment 40 and filled with medication 116. Thus, in this embodiment, a self-contained medication chamber 112 is provided which is pre-charged and filled with medication 116 within the treatment tube/catheter's wall 32 adjacent each medication diffusion segment 40.

Within each hollow medication chamber 112 is a solid interior wall segment 114 formed as an extension of the treatment tube/catheter's wall 32 extending into the hollow medication chambers 112 having open peripheral edges 118 which are spaced from the corresponding side cross-sectional interior walls 120 of the medication chamber 112 thus permitting medication to freely flow around the open peripheral edges 118 and the side cross sectional periphery of the interior wall segment 114.

An expandable capsule 124 is disposed within the medication chamber 112 in between the lower peripheral edge 118 of the interior wall segment 114 and the adjacent lower interior wall 120 of the medication chamber.

In one embodiment, the capsule 124 includes a single chamber with a material which expands upon exposure to liquid such as an expandable foam 126. The capsule 124 also includes medicine ingress ports 128 at either end of the capsule's 124 chamber, wherein upon introduction of the liquid medication into the capsule 124 containing the expandable foam 126 via the ports 128, the foam 126 expands within the chamber 112 and the outward, axial expansion of the foam 126 within the space in between the lower peripheral edge 118 of the interior wall segment 114 and the adjacent lower interior wall 120 of the medication chamber toward the outer peripheral edges 118 of the solid interior wall segment 114 displaces or pushes the liquid medication 116 contained within the self-contained chamber 112 around the peripheral edges 118 of the interior wall segment 114 and out of the apertures 52 or micropores 56 of the medication diffusion segment 40 to be administered to the surrounding pain-sensitive tissues and membranes. In this manner, the solid interior wall segment 114, working in concert with the expandable capsule 124, creates pressure within the medication chamber 112 for the delivery and administration of medication.

In one embodiment, the ports 128 are activated and opened by pressure or deformation of the capsule 124 just prior to insertion of the treatment tube/catheter within the patient's body such that bending or deformation of the treatment tube/catheter 22 along the medication chamber 112 in the vicinity of the capsule 124 causes ports 128 to be broken or opened, permitting the foam 126 to expand via the exposure to the liquid medication 116 to gradually and consistently push the medication 116 from within each medication chamber 112 through the apertures 52 or micropores 56 of the medication diffusion segment 40.

Alternatively, the capsule 124 includes two expandable chambers 130, each chamber 130 attached to the other at the inner ends 134 of the chambers 130. Furthermore, each chamber 130 includes an expandable spring 136 tethered between and affixed at the spring's ends to the fixed inner end 134 and the outer end 138 of each chamber 130 such that upon activation of the capsule 124, the springs 136 expand against the fixed inner ends 134 of each chamber 130 thereby causing the outer ends 138 to expand and move axially outward and away from the fixed inner ends 134 of each chamber 130 to displace or push the liquid medication 116 contained within the self-contained chamber 112 out of the apertures 52 or micropores 56 in a like manner as described above. In either version of this embodiment, the expansion of the foam 126 or alternatively, the expandable, spring-loaded chambers 130 provides a constant diffusion of medication 116 over a specific time period, which in one embodiment is 24 hours, until all the medication 116 within the chamber 112 has been delivered to the pain sensitive mucous membranes and tissues, while at the same time eliminating the need to externally deliver medication into the conduits 24 via the connections to the medication delivery system's 12 pump 16 and connecting conduit 18.

In a fifth embodiment of the apparatus and system for administering medication 10, each of the one or more medication diffusion segments includes separate, discrete groups of apertures 54 comprised of a proximal group of apertures 140, at least one middle group of apertures 142, and a distal group of apertures 144 extending through the treatment tube/catheter 22 wall into each hollow tubular channel 42. In one embodiment, each group of apertures 140, 142, 144 includes a linear array or series of three equally spaced, adjacent apertures 54. Alternatively, each group of apertures 140, 142, 144 includes two or more equally spaced, adjacent apertures. Additionally, the second/distal end 68 of the medication delivery conduit 24 is closed such that no liquid medication is permitted to flow from the conduit's distal end. The second/distal end 58 of the medication delivery conduit 24 also includes a single array of equally spaced, adjacent apertures 146 having a size, width, and spacing which corresponds to and aligns with the proximal 140, middle 142, and distal groups of apertures 144 of each medication diffusion segment 40 such that upon insertion of the each of the one or more medication delivery conduit's second/distal ends 68 into each hollow tubular channel 42, the position of each conduit's distal end 68 and single array of apertures 146 can be adjusted axially at various positions within each hollow tubular channel 42 to align with and deliver liquid medication to a single group of corresponding apertures 140, 142, 144, thereby providing a variable, site specific administration of pain medication from the medication delivery conduit 24 into and through a specific group of apertures 140, 142, 144 to pain-sensitive tissues adjacent the medication administration section 38 of the treatment tube/catheter 22 at any one of a variety of specific positions along each of the medication diffusion segments 40.

An adjustable lattice sleeve 148 is also provided which fits snugly around the exterior surface 34 of the treatment tube/catheter 22. The adjustable lattice sleeve 148 includes one or more medication profusion segments 150 wherein each medication profusion segment 150 is an axial segment of the sleeve's 148 body comprised of a network or lattice of micropores 152, which, upon the introduction of liquid medication to the lattice of micropores 152, the liquid medication is disbursed and communicated throughout the entire surface area of the medication profusion segment 150 via the network of latticed micropores 152. In one embodiment, the sections of the lattice sleeve's 148 body in between the profusion segments 150 is comprised of an elastic material that allows the lattice sleeve 148 to be slid along the treatment tube/catheter's exterior surface 34 while at the same time maintaining a snug, secure engagement between the sleeve 148 and the tube/catheter 22 once the sleeve 148 has been positioned. Each of the one or more medication profusion segments 150 is positioned on the body of the adjustable lattice sleeve 148 to align axially with and cover each corresponding medication diffusion segment 40 along the exterior surface 34 of the treatment tube/catheter's wall 32. However, in a preferred embodiment, the width of each medication profusion segment 150 (represented as the amount of the circumference of the adjustable lattice sleeve 148 occupied by each medication profusion segment 150) is greater than the width of each corresponding medication diffusion segment 40 and the diameter of the apertures 54 provided therein. Thus, with the adjustable lattice sleeve 148 positioned around the medication administration segment 38 and each medication profusion segment 150 aligned axially adjacent to each medication diffusion segment 40, liquid medication supplied to the medication profusion segments 150 from the diffusion segment's apertures 40 is distributed throughout a larger surface area around the exterior circumference of the treatment tube/catheter's exterior surface 32 via the micropores 152 of the medication profusion segments 150.

In the instant embodiment, the axial length of each of the medication profusion segments 150 is equivalent to, or alternatively, is slightly longer than that of each individual group of apertures 140, 142, 144 such that the position of the lattice sleeve 148 can be adjusted proximally or distally along the treatment tube/catheter's exterior surface 34 as the sleeve 148 is slid along the medication administration section 38 to align with and further disperse liquid medication adjacent a proximal, middle, or distal group of apertures 140, 142, 144 through which liquid medication is being delivered.

Furthermore, in addition to the first, second and third indicator marks 82, 84, and 86 and the corresponding first, second, and third sets of printed indicia 76, 78, 80, respectively, in this embodiment each of the proximal, middle, and distal individual groups of apertures 140, 142, 144, include an adjacent third, fourth, and fifth indicator marks, 154, 156, 158, respectively, and accompanying, corresponding third, fourth, and fifth sets of printed indicia 160, 162, 164 to provide proper alignment and placement of the individual groups of apertures 140, 142, 144 with respect to the pain sensitive tissues as the treatment tube/catheter assembly 14 is being inserted into the patient's body, as described above.

Notwithstanding, the use of the adjustable lattice sleeve 148 is not limited to the instant embodiment, and the axial width of the medication profusion segments 150 alternatively is equivalent to, or is slightly longer than the axial width of the entirety of each of the one or more medication diffusions segments 40 as disclosed in any of the foregoing embodiments.

In the manner described by any or all of the foregoing embodiments, an apparatus and system for administering medication 10 has been disclosed which provides a continuous flow of site-specific pain medication directly to the source of the pain caused by a foreign body. The system also decreases the surface area of the tube in contact with the pain sensitive membranes, administers the most amount of pain medication to the most sensitive areas of the patient to therefore provide more effective, targeted, and responsive pain control, provides a controlled, even distribution of pain medication, and provides a greater degree of contact and distribution between the pain sensitive membranes and the pain medication. As a result at the very least all of the stated objectives have been met.

It will be appreciated by those skilled in the art that other various modifications could be made to the device without the parting from the spirit and scope of this invention. All such modifications and changes fall within the scope of the claims and are intended to be covered thereby.

What is claimed is:

1. An apparatus for administering medication comprising:
   a treatment tube;
   the treatment tube extending a length between a proximal end and a distal end;
   the treatment tube having a wall with an exterior surface and a central lumen extending the length of the treatment tube;
   at least one hollow tubular channel disposed within the wall of the treatment tube;
   the hollow tubular channel extending a length from a proximal end to a distal end;
   a medication diffusion segment positioned in the wall of the treatment tube adjacent the distal end of the hollow tubular channel and in communication with the hollow tubular channel;
   wherein the hollow tubular channel is configured to deliver medication through the medication diffusion segment to the exterior surface of the treatment tube;
   wherein the medication diffusion segment has a series of apertures;
   a recessed segment positioned in the wall of the treatment tube;
   a medication delivery conduit connected to the hollow tubular channel and wrapped helically around the recessed segment in the wall of the treatment tube.

2. The apparatus for administering medication of claim 1 wherein the medication delivery conduit has a central lumen and is configured to deliver medication to the treatment tube's hollow tubular channel.

3. The apparatus for administering medication of claim 2 wherein the medication delivery conduit includes a series of apertures.

4. The apparatus for administering medication of claim 3 wherein the medication delivery conduit includes a medication delivery segment having apertures at a distal end of the medication delivery conduit.

5. The apparatus for administering medication of claim 4 wherein the medication delivery segment is received within the hollow tubular channel.

6. The apparatus for administering medication of claim 1 wherein the portion of the medication delivery conduit positioned within the recessed segment of the treatment tube includes apertures.

7. The apparatus for administering medication of claim 6 wherein the medication is delivered through apertures that increase in size from the proximal end to the distal end of the hollow tubular channel.

8. The apparatus for administering medication of claim 1 further comprising an axial groove positioned within the recessed segment that holds the medication delivery conduit.

9. The apparatus for administering medication of claim 1 further comprising measurement markings positioned in the exterior surface of the treatment tube.

10. The apparatus for administering medication of claim 1 wherein the series of apertures of the medication diffusion segment gradually increase in size as they extend from the proximal end to the distal end of the hollow tubular channel.

11. A method of administering medication comprising the steps of:
    providing a treatment tube, wherein the treatment tube extends a length between a proximal end and a distal end, the treatment tube having a wall with an exterior surface and a central lumen extending a length of the treatment tube, at least one hollow tubular channel disposed within the wall of the treatment tube, wherein the hollow tubular channel extends a length from a proximal end to a distal end, a medication diffusion segment positioned in the wall of the treatment tube adjacent the distal end of the hollow tubular channel and in communication with the hollow tubular channel, the treatment tube also having a recessed segment positioned in the wall of the treatment tube;
    spacing the medication diffusion segment proximally a distance from the distal end of the treatment tube;
    placing the treatment tube into a patient's body;
    positioning the medication diffusion segment adjacent pain sensitive tissues of the patient's body;
    wrapping a medication delivery conduit around the recessed segment positioned in the wall of the treatment tube;
    connecting the medication delivery conduit to the hollow tubular channel; and
    using the central lumen for a first medical procedure while simultaneously delivering pain medication into the one or more hollow tubular channels through the wall of the treatment tube to the patient's adjacent pain sensitive tissues.

12. The method for administering medication of claim 11 additionally including the step of providing measurement markings in the exterior surface of the treatment tube.

13. The method for administering medication of claim 11 additionally including the step of inserting the medication delivery conduit into the wall of the treatment tube to supply the at least one hollow tubular channel.

14. An apparatus for administering medication comprising:
- a treatment tube;
- the treatment tube extending a length between a proximal end and a distal end;
- the treatment tube having a wall with an exterior surface and a central lumen extending the length of the treatment tube;
- a port positioned in the exterior surface of the treatment tube;
- a first hollow tubular channel disposed within the wall of the treatment tube;
- a first medication diffusion segment positioned in the wall of the treatment tube adjacent a distal end of the first hollow tubular channel and in communication with the first hollow tubular channel;
- a second hollow tubular channel disposed within the wall of the treatment tube;
- a second medication diffusion segment positioned in the wall of the treatment tube adjacent a distal end of the second hollow tubular channel and in communication with the second hollow tubular channel;
- wherein the first hollow tubular channel and the second hollow tubular channel are connected to the port by an intermediate channel;
- wherein the intermediate channel is positioned within the wall of the treatment tube, such that the intermediate channel branches out into the first hollow tubular channel and the second hollow tubular channel;
- wherein the first hollow tubular channel and the second hollow tubular are configured to deliver medication through the medication diffusion segments to the exterior surface of the treatment tube.

15. The apparatus for administering medication of claim 14 wherein the first hollow tubular channel and the second hollow tubular channel are spaced away from one another around the circumference of the treatment tube.

16. The apparatus for administering medication of claim 14 further comprising measurement markings positioned in the exterior surface of the treatment tube.

17. The apparatus for administering medication of claim 14 wherein the first medication diffusion segment and second medication diffusion segment are spaced proximally a distance from the distal end of the treatment tube, such that when the treatment tube is inserted within a patient's body, the central lumen is configured for use with a first medical procedure while the first medication diffusion segment and second medication diffusion segment is positioned adjacent pain sensitive tissues of the patient's body.

18. An apparatus for administering medication comprising:
- a main treatment tube;
- the main treatment tube extending a length between a proximal end and a distal end;
- the main treatment tube having a wall with an exterior surface and a central lumen extending within the main treatment tube;
- at least one hollow tubular channel disposed within the wall of the main treatment tube;
- the hollow tubular channel extending a length from a proximal end to a distal end;
- an insertion opening positioned in the exterior surface of the main treatment tube and connected to the proximal end of the hollow tubular channel;
- a medication diffusion segment positioned in the wall of the treatment tube adjacent the distal end of the hollow tubular channel and in communication with the hollow tubular channel; and
- wherein the hollow tubular channel is configured to deliver medication through the medication diffusion segment to the exterior surface of the treatment tube;
- a recessed segment positioned in the wall of the main treatment tube;
- a medication delivery conduit connected to the hollow tubular channel and wrapped helically around the recessed segment in the wall of the main treatment tube.

* * * * *